(12) United States Patent
Shi et al.

(10) Patent No.: US 8,853,399 B1
(45) Date of Patent: Oct. 7, 2014

(54) BIPYRIDINE TRIAZOLE TYPE RARE EARTH COMPLEX AND PREPARATION METHOD THEREOF

(71) Applicant: Guangdong Synyoo New Material Co., Ltd., Foshan (CN)

(72) Inventors: Huahong Shi, Foshan (CN); Jiguo Song, Foshan (CN); Hangbing Fang, Foshan (CN); Dong Liang, Foshan (CN); Shangen Ning, Foshan (CN)

(73) Assignee: Guangdong Synyoo New Material Co., Ltd., Foshan (CN)

( * ) Notice: Subject to any disclaimer, the term of this patent is extended or adjusted under 35 U.S.C. 154(b) by 0 days.

(21) Appl. No.: 14/356,775

(22) PCT Filed: Jun. 17, 2013

(86) PCT No.: PCT/CN2013/077288
§ 371 (c)(1),
(2), (4) Date: May 7, 2014

(87) PCT Pub. No.: WO2014/000581
PCT Pub. Date: Jan. 3, 2014

(30) Foreign Application Priority Data

Jun. 28, 2012 (CN) .................... 20 1210 219 952 U
Jan. 8, 2013 (CN) .................... 20 1310 006 548 U (51) Int. Cl.
*C07F 19/00* (2006.01)
*C07F 5/00* (2006.01)

(52) U.S. Cl.
CPC ...................................... *C07F 5/003* (2013.01)
USPC .......................................................... 546/2

(58) Field of Classification Search
USPC .......................................................... 546/2
See application file for complete search history.

(56) References Cited

U.S. PATENT DOCUMENTS

2011/0112289 A1  5/2011  Giraud et al.

FOREIGN PATENT DOCUMENTS

| CN | 1834094 A | 9/2006 |
| CN | 103044466 A | 4/2013 |
| CN | 103172649 A | 6/2013 |

OTHER PUBLICATIONS

G. F. de Sa et al., "Spectroscopic properties and design of highly luminescent lanthanide coordination complexes", Coordination Chemistry Reviews, 196 (2000) pp. 165-195.
International Search Report for PCT/CN2013/077288, Mailing Date of Oct. 3, 2013.

*Primary Examiner* — Charanjit Aulakh

(74) *Attorney, Agent, or Firm* — Westerman, Hattori, Daniels & Adrian, LLP

(57) ABSTRACT

A bipyridine triazole rare earth complex $LnL_3$ as shown in Formula 1 and a preparation method thereof. The rare earth complex has high thermal stability and is suitable for manufacturing devices by an evaporation film-forming process or manufacturing devices by a solution film-forming process. The preparation method has the advantages of high yield, good product purity, short reaction time and simplicity in operation, and can greatly reduce cost.

Formula 1

-continued

8 Claims, 2 Drawing Sheets

BIPYRIDINE TRIAZOLE TYPE RARE EARTH COMPLEX AND PREPARATION METHOD THEREOF

FIELD OF THE INVENTION

The invention relates to a novel bipyridine triazole type rare earth complex and a preparation method thereof.

BACKGROUND OF THE INVENTION

China is exceptionally rich in resources to develop applications of rare earth. In the currently ascertained rare earth resources around the world, 80% of the rare earth resources exist in China and the varieties are complete. In order to protect the resources and avoid the environmental problems caused by excessive development, China has began to manage and control the export of rare earth ore since 2009, but this action was protested by America, Japan, Europe and other countries. This reflects the preciousness of the rare earth resources and the necessary and the urgency in great development of deep processing of rare earth from another perspective. Directed to rich and distinctive rare earth resources in China, the optical materials which are the most distinctive rare earth elements and have been well accumulated in China are taken as the main development direction in the transition of Chinese rare earth industry to high-tech functional material industry, which per se also reflects the great industrial development requirements of China.

Organic electroluminescence is self-luminescent and has luminescent materials rich in colors for selection, and thus has the advantages of high efficiency, high brightness (>10,000 cd/m$^2$), high contrast (>1000:1), wide color gamut (>100% NTSC), wide viewing angle (0-180°), fast response (microsecond grade) and the like in the properties of display and luminescence, and furthermore, light, thin (less than 1 mm) and flexible display is realized, and these performances exceed those of all the existing display technologies, so that the organic electroluminescence is generally acknowledged as the next generation of flat panel display technologies and lighting technologies.

Central luminescent ions of the rare earth complex can be divided into visible region strongly-luminescent rare earth ions, weakly-luminescent rare earth ions, rare earth ions with f-d radiation transitions and visible region non-luminescent rare earth ions. For example. $Eu^{2+}$, $Ce^{3+}$ and $Tm^{3+}$ emit blue light. $Eu^{3+}$ emits red light, $Tb^{3+}$ emits green light, $Sm^{3+}$ emits pink light, $Dy^{3+}$ emits yellow light and $Nd^{3+}$, $Er^{3+}$ and $Yb^{3+}$ emit near-infrared light. The radiation transitions of $Tb^{3+}$ and $Eu^{3+}$ fall within a visible light region, and during research of luminescent materials of the rare earth complex, the two types of ions attract the most attention, wherein a main emission peak of $Tb^{3+}$ is positioned at about 545 nm and the color is very pure green; and the main emission peak of $Eu^{3+}$ is positioned at about 613 nm, and the color is red with great eye sensitivity. The sensitized luminescence property of the rare earth can be applied to OLED display/lighting technologies in practices, biomedical test and anti-counterfeiting label printing, as well as infrared communication technologies. Since 1990, Kido team has firstly proved that β-diketone complexes of terbium can be used as luminescent materials for OLED devices. As they have narrow emission peaks and half-peak width of less than 10 nm, the chroma is saturated and bright, and the photo-quantum efficiency of rare earth organic luminescent materials is ultrahigh, the photo-quantum efficiency of reported solid europium complexes can achieve 85% (*Coordination Chemistry Reviews*, 2000, 196: 165), and the development of the rare earth organic luminescent materials re-attracts high attention of scientific community. The OLED devices of the europium complexes can obtain red light with saturated chroma; and the OLED devices of the terbium complexes can obtain green light with pure chroma. However, the efficiency and the service life of these devices fall far behind their theoretical expectations. The main reasons comprise poor film-forming ability of small molecular rare earth complexes, poor transmission performance of a current carrier and poor electrical, optical and thermal stability. As for other types of luminescent materials, such as small molecular organic luminescent materials, high polymer luminescent materials, complexes of precious metals, such as iridium, platinum and gold, and the like, although the emission peaks are wide, and the half-peak width is generally 80-100 nm, the color is dim in comparison with the rare earth luminescent materials; however, the efficiency and the service life of these luminescent materials have achieved the practical requirements.

The rare earth element needs 9-coordination to achieve saturated coordination; and simultaneously, as the rare earth metal ions have positive charges, ligands need to have negative charges to meet electrical neutrality. So far, the rare earth complex luminescent materials have adopted mixed ligands, e.g. 1,10-phenanthroline, β-diketone, and pyridine carboxylic acid compounds as ligands or for providing negative charges.

Up till now, novel rare earth luminescent complexes which are suitable for actual applications and even suitable for OLED display and lighting technologies have not been reported.

SUMMARY OF THE INVENTION

The invention aims at providing a novel bipyridine triazole rare earth complex. Another purpose of the invention is to provide a preparation method of the novel bipyridine triazole type rare earth complex.

The invention is implemented through the following technical scheme:

The structural formulas of the bipyridine triazole type rare earth complex $LnL_3$ are as shown in formula 1:

Formula 1

2

3

4 wherein R₁ is selected from hydrogen, halogen, an alkane group or an aromatic hydrocarbon group; R₂ is selected from hydrogen, halogen, an alkane group or an aromatic hydrocarbon group; R₃ is selected from hydrogen, halogen, methyl, trifluoromethyl or phenyl; and central rare earth ions Ln are selected from any one of yttrium, lanthanum, cerium, praseodymium, neodymium, samarium, europium, gadolinium, terbium, dysprosium, holmium, erbium, thulium, ytterbium and lutetium. The synthesis method of the bipyridine triazole type rare earth complex, provided by the invention, comprises the following steps:

a) oxidizing a bipyridine derivative as shown in structural Formula 2 by an oxidant to generate a bipyridine type nitrogen oxide;

b) performing cyano-substitution on the bipyridine type nitrogen oxide to obtain a 6-cyano-bipyridine derivative;

c) enabling the 6-cyano-bipyridine derivative to react with hydrazine and a carboxylic acid derivative for cyclization, thus obtaining a bipyridine triazole type compound; and d) enabling a rare earth metal salt to react with the bipyridine triazole type compound to generate the bipyridine triazole type rare earth complex $LnL_3$.

Formula 2

The reaction expression is as follows:

As for the oxidation reaction in step a), the oxidant is selected from m-chloroperoxybenzoic acid (m-CPBA) or hydrogen peroxide solution; the molar ratio of the oxidant to the bipyridine derivative is not less than 1:1; the reaction temperature is from room temperature to 110° C.; and a solvent is selected from carboxylic acid or alkyl halide, and the minimal using amount of the solvent needs to just dissolve the raw materials.

As for step b), a cyano (CN) reagent is selected from NaCN, KCN, CuCN, Zn(CN)$_2$ or (CH$_3$)$_3$SiCN (TMSCN, trimethylsilyl cyanide); the reaction is temperature-sensitive, and the temperature needs to be controlled to be less than 80° C.; and the reaction time is 1-7 days according to different reaction substrates.

The reaction in step c) can be implemented by adopting the following two ways:

(1) enabling the hydrazine to react with 6-cyano-2,2'-bipyridine derivative in a mixed solvent of alcohol and water in the volume ratio of 1:0 to 0:1, and then reacting with carboxylic acid, acid anhydride, acyl chloride or ester in a halogenated alkane, ester, aromatic hydrocarbon, alcohol, acid or ether solvent for cyclization, wherein the using amount of the hydrazine is not less than 1.0 equivalent, the using amount of the carboxylic acid, acid anhydride, acyl chloride or ester is not less than 1.0 equivalent, and the minimal using amount of the solvent is proper to be sufficient to dissolve the raw material; and the reaction temperature ranges from room temperature to reflux temperature according to different reaction substrates; and (2) enabling the 6-cyano-2,2'-bipyridine derivative and acylhydrazine to react directly in the halogenated alkane, ester, aromatic hydrocarbon, alcohol, acid or ether solvent for cyclization, and the minimal using amount is proper to be sufficient to dissolve the raw material; and the reaction temperature ranges from room temperature to reflux temperature according to different reaction substrates.

Preferably, as for the reaction in step c), the 6-cyano-bipyridine derivative is firstly dissolved in an organic solvent, the temperature is controlled at −20° C. to 50° C., the hydrazine and the carboxylic acid derivative, which are dissolved in the organic solvent are dropped, the reaction is further performed for 1-24 h after the end of dropping, the product is crystallized, filtered and recrystallized to obtain the bipyridine triazole type compound, and the organic solvent is selected from ether, ester, aromatic hydrogen, alcohol, acetonitrile or ketone.

As for the reaction in step d), the rare earth metal salt is dissolved in water and dropped into a solution of the bipyridine triazole type compound and a water-soluble organic solvent of an alkali, the temperature is controlled at 0° C.-100° C., the reaction is continuously performed for 1-48 h after the end of dropping, and the product is filtered and recrystallized to obtain the bipyridine triazole type rare earth complex LnL$_3$; and the organic ligand bipyridine triazole derivative firstly react with the alkali and then the reactant is mixed with the rare earth metal salt solution for reaction to obtain the bipyridine triazole type rare earth complex.

The rare earth metal salt is selected from chloride, bromide, fluoride, iodide, nitrate, sulfate, perchlorate, phosphate, carboxylate, sulfonate, fluoroborate and hexafluorophosphate; the using amount of the rare earth metal slat is 1.0 equivalent, the using amount of the bipyridine triazole derivative is 2.0-4.0 equivalents, preferably 3.0 equivalents, the alkali is inorganic alkali or organic alkali, and the using amount is not less than 1.0 equivalent; and the organic solvent can be various alcohols selected from ROH, 2-ethoxyethanol, 2-methoxyethanol, 1,3-propanediol, 1,2-propanediol, ethylene glycol or glycerol; and the volume ratio of the organic solvent to the water in the water-soluble organic solvent is 1:0 to 0:1.

As for the bipyridine triazole type rare earth complex, if Ln is europium, red light is emitted, and the main peak of an emission spectrum is 621 nm; while terbium emits green light of which the main peak is 545 nm; thulium emits blue light of which the main peak is 470 nm; samarium emits pink light of which the main peak is 640 nm; dysprosium emits yellow light of which the main peak is 570 nm; and neodymium, erbium and ytterbium emit infrared lights of which the main peaks are 1065 nm, 1509 nm and 978 nm respectively.

The invention is different from the prior art in the following aspects: the bipyridine triazole type tridentate compound is adopted as a single ligand, the coordination saturation is simultaneously met, and a triazole group in the complex is taken as negative ions to realize charge balance with the central rare earth metal positive ions so as to realize electrical neutrality. As the ligand is in tridentate coordination chelating with the rare earth ions, the rare earth complexes have high thermal and electrical stability and are suitable for being manufactured into devices by an evaporation film-forming process; and in addition, by modification of R$_1$, R$_2$ or R$_3$, the rare earth complexes which are easy to dissolve in an organic solvent and even water are synthesized, and the rare earth complexes are also suitable for being manufactured into devices by a solution film-forming process.

The preparation method of the invention has the advantages of high yield, good product purity, short reaction time and simplicity in operation, and can greatly reduce cost.

DETAILED DESCRIPTION OF THE INVENTION

The following embodiments are used for further describing rather than limiting the invention.

Embodiment 1

Synthesis of tri[5-(2,2'-bipyridine-6-yl)-1,2,4-1H-triazole]europium (III) (compound 6)

The first step: preparation of N-oxo-2,2'-bipyridine (compound 2)

Firstly, adding a compound (1) 2,2'-bipyridine (100 g) and acetic acid (500 mL) into a 2 L three-necked flask, uniformly stirring, adding 30% H₂O₂ (70 mL), heating to 70-75° C., and stirring to reaction for 3 h; cooling to room temperature, adding 30% H₂O₂ (70 mL), continuously heating to 60-110° C. and reacting for 3 h; cooling to room temperature, performing vacuum concentration to remove the acetic acid so as to obtain a reddish brown viscous oily substance, diluting with water (1000 mL), and regulating the pH to 8-9 by using solid sodium carbonate; extracting an obtained solution by using dichloromethane (1000 mL+500 mL×3), mixing organic phases, and drying by using anhydrous sulfuric acid; and filtering, increasing pressure for concentration on filtrate to obtain the reddish brown oily substance, and directly putting the oily substance into the next-step reaction without purification.

The second step: preparation of 6-cyano-2,2'-bipyridine (compound 3)

Firstly, dissolving the oily substance (compound 2) obtained in the previous step in 500 mL of dichloromethane, transferring into the 2 L three-necked flask, and cooling to below 10° C. by an ice-water bath; dropping trimethylsilyl cyanide (TMSCN, 200 mL), and keeping the internal temperature below 25° C.; reacting by the ice-water bath for half an hour after the end of dropping; dropping benzoyl chloride (60 mL), and keeping the internal temperature below 25° C.; reacting for 72 h at room temperature after the end of dropping; cooling by an ice-salt bath to lower the internal temperature to below 0° C.; dropping a saturated sodium hydrogen carbonate solution (1000 mL), keeping the internal temperature below 10° C. and stirring at room temperature to react for 1 h after the end of dropping; then loading a reaction system into a 5 L separatory funnel, and adding the dichloromethane (2000 mL); washing an organic layer with water (1000 mL×3), then washing with saturated brine (1000 mL×2), and drying with anhydrous sodium sulfate; filtering out a drying agent; increasing pressure for concentration and drying to obtain off-white semi-solids, and stirring and washing for 4 h by using 500 mL of petroleum ether; filtering, and washing a filter cake with the petroleum ether (100 mL); and performing vacuum drying on obtained white powder at the temperature of 40° C. for 8 h to obtain 70 g of white solid powder.

MS: [M+1] 181.9, C11H7N3 M.W.=181, and 182 (M+H peak) and 204 (M+Na peak) are detected.

The third step: preparation of 5-(2,2'-bipyridine-6-yl)-1,2,4-1H-triazole (compounds 4 and 5)

Adding the compound 3 (70 g), anhydrous ethanol (1000 mL) and hydrazine hydrate (80%, 200 mL) into the 2 L three-necked flask, stirring at room temperature to react for 8 h, and freezing a reaction solution in a refrigerator for 16 h; filtering out solids, washing with cold ethanol (100 mL), and draining; and directly putting obtained needle-like light yellow crystals into reaction without drying;

adding 80% formic acid (1000 mL) into the 2 L three-necked flask, cooling to below 0° C. by an ice-salt bath, then adding the above needle-like crystals in batches, and keeping the internal temperature below 5° C.; reacting for 1 h under ice bath conditions after the end of adding; performing heating and reflux reaction for 2 h; cooling to room temperature; removing a solvent by concentration; diluting obtained residues with water (1000 mL); regulating the pH to about 9 by using sodium carbonate solids, and extracting with ethyl acetate (1000 mL+500 mL×2); mixing organic phases, and drying with anhydrous sodium sulfate; filtering out the drying agent; increasing pressure for concentration and drying to obtain off-white semi-solids, and stirring and washing for 16 h by using petroleum ether:ethyl acetate=20:1 (V:V) (500 mL); filtering, draining, and washing a filter cake with the petroleum ether (100 mL); and performing vacuum drying on the filter cake at the temperature of 40° C. for 8 h to obtain 40 g of white solid powder.

¹HNMR (400 MHz, DMSO), ppm: 7.52 (1H, t), 8.01 (1H, t), 8.14 (2H, m), 8.33 (1H, s), 8.50 (1H, m), 8.74 (1H, d) and 8.84 (1H, d).

MS: [M+1] 224.1, C12H9N5 M.W.=223, and 224 (M+H peak) and 246 (M+Na peak) are detected.

The fourth step: preparation of tri[5-2,2'-bipyridine-6-yl)-1,2,4-1H-triazole]europium (III) (compound 6) and fluorescence emission spectrum test EuCl3 6H2O →(Ethanol/H2O 1:3)

6

Dissolving the compound 4 (6.7 g) and europium (1H) chloride hexahydrate (3.7 g) respectively in 50 mL of a mixed solvent of anhydrous ethanol:water (V:V)=1:3 to prepare a solution A and a solution B: adding 1.2 g of sodium hydroxide into the solution A, and stirring to react for half an hour; then dropping the solution B into a reaction flask of the solution A, and stirring at room temperature to react for 8 h; and reducing pressure for evaporation after the end of reaction to remove the solvent, performing vacuum drying on the solids at the temperature of 50° C. for 3 h to obtain 9.5 g of light yellow green powder.

Figure 1:
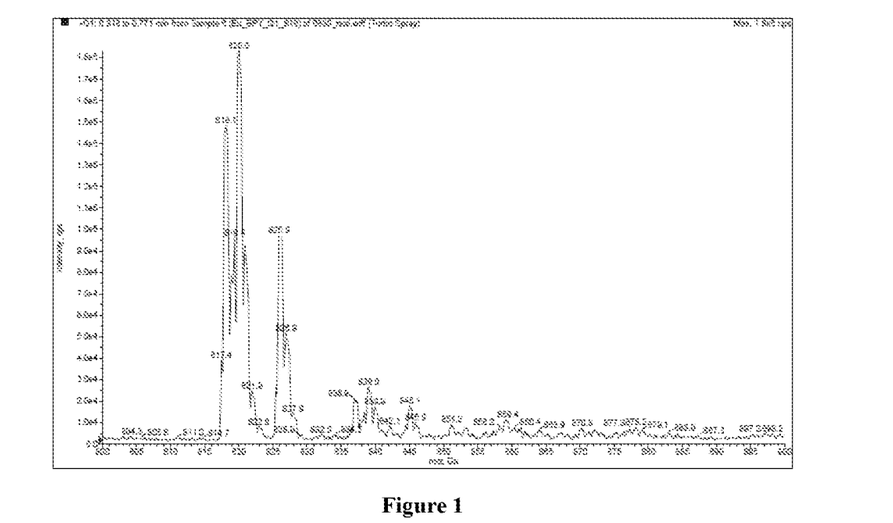
FIG. 1 is a mass spectrogram of tri[5-(2,2'-bipyridine-6-yl)-1,2,4-1H-triazole]europium (II).

MS: [M+1] 820.0, EuC36H24N15 M.W.=818, and the peak height ratio of M+H peak 818: M+H peak 820 is detected to be close to the isotopic abundance ratio of Eu, namely 1:1. The mass spectrogram is as shown in FIG. 1.

Through fluorescence emission spectrum test, we can know that the fluorescence emission wavelengths of the tri[5-(2,2'-bipyridine-6-yl)-1,2,4-1H-triazole]europium (III) are 592 nm and 618 nm.

Embodiment 2

Synthesis of tri[5-(2,2'-bipyridine-6-yl)-1,2,4-1H-triazole]terbium (III) (compound 7) and fluorescence emission spectrum test

4

TbCl3 6H2O →(Ethanol/H2O 1:3)

7

Dissolving the compound 4 (7.4 g) prepared in the previous embodiment and terbium (III) chloride hexahydrate (3.7 g) respectively in 50 mL of a mixed solvent of anhydrous ethanol:water (V:V)=1:3 to prepare a solution C and a solution D; adding 1.2 g of sodium hydroxide into the solution C, and stirring to react for half an hour; then dropping the solution D into a reaction flask of the solution C, and stirring at room temperature to react for 8 h; and reducing pressure for evaporation after the end of reaction to remove the solvent, performing vacuum drying on solids at the temperature of 50° C. for 3 h to obtain 9.3 g of yellow powder.

Figure 2:
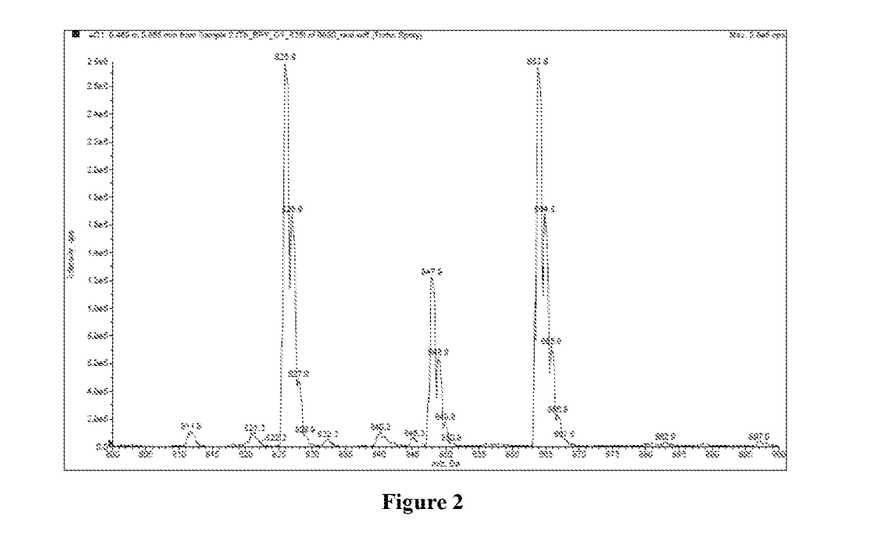
FIG. 2 is a mass spectrogram of tri[5-(2,2'-bipyridine-6-yl)-1,2,4-1H-triazole]terbium (III).

MS: [M+1] 825.9, TbC36H24N15 M.W.=825, and the peak height ratio of M+H peak 826:827 is detected to be close to the isotopic abundance ratio of Tb, namely 2:1. The mass spectrogram is as shown in FIG. 2.

Through fluorescence emission spectrum test, we can know that the fluorescence emission wavelengths of the tri[5-(2,2'-bipyridine-6-yl)-1,2,4-1H-triazole]terbium (III) are 490 nm, 544 nm, 586 nm and 623 nm.

Embodiment 3

Synthesis of tri[5-(4,4'-dibromo-2,2'-bipyridine-6-yl)-1,2,4-1H-triazole]terbium (III) (compound 13) and fluorescence emission spectrum test The first step: preparation of N-oxo-4,4'-dibromo-2,2'-bipyridine (compound 9)

Firstly, adding 4,4'-dibromo-2,2'-bipyridine (compound 8, 200 g) and trichloromethane (800 mL) into a 2 L three-necked flask, uniformly stirring, cooling to 0° C., and slowly dropping a trichloromethane (600 mL) solution of m-chloroperoxybenzoic acid (180 g); continuously heating to room temperature, and stirring to react for 3 h; continuously heating to 60° C. and further reacting for 3 h; cooling to room temperature, performing vacuum concentration to remove the trichloromethane, diluting with water (1000 mL), and regulating the pH to 8-9 by using solid sodium carbonate; removing the raw material 4,4'-dibromo-2,2'-bipyridine which does not completely react in a mixture by heating to 90-95° C. for half an hour, cooling and performing suction filtration; extracting obtained filtrate by using dichloromethane (1000 mL+500 mL×3), mixing organic phases, and drying by using anhydrous sulfuric acid; and filtering, concentrating and recrystallizing by using petroleum ether to obtain 169 g of light grey solids.

The second step: preparation of 6-cyano-4,4'-dibromo-2,2'-bipyridine (compound 10)

Firstly, dissolving the product (compound 9, 73 g) obtained in the previous step in 500 mL of dichloromethane, transferring into the 2 L three-necked flask, and cooling to below 10° C. by an ice-water bath; dropping trimethylsilyl cyanide (TMSCN, 250 mL), and keeping the internal temperature below 15° C.; reacting by the ice-water bath for 1 h after the end of dropping; dropping benzoyl chloride (50 mL), and keeping the internal temperature below 15° C.; reacting for 72 h at room temperature after the end of dropping; cooling by an ice-salt bath to lower the internal temperature to below 0° C.; dropping a saturated sodium hydrogen carbonate solution (1000 mL), keeping the internal temperature below 10° C. and stirring at room temperature to react for 1 h after the end of dropping; then loading a reaction system into a 5 L separatory funnel, and adding the dichloromethane (2000 mL); washing an organic layer with water (1000 mL×3), then washing with saturated brine (1000 mL×2), and drying with anhydrous sodium sulfate; filtering out a drying agent; increasing pressure for concentration and drying to obtain flesh pink solids; and recrystallizing by using 1000 mL of ethanol, filtering, washing, and performing vacuum drying at the temperature of 50° C. for 8 h to obtain 56 g of grey solids.

MS: [M−1] 337.9. C11H5Br2N3 M.W.=339, and the peak height ratio of M−H peak 336:338:340 is detected to be close to 1:2:1, which is in line with the number of atoms and the isotopic abundance ratio of Br.

The third step: preparation of 5-(4,4'-dibromo-2,2'-bipyridine-6-yl)-1,2,4-1H-triazole (compounds 11 and 12)

Adding the compound 10 (50 g), anhydrous ethanol (500 mL) and hydrazine hydrate (80%, 50 mL) into the 2 L three-necked flask, stirring at room temperature to react for 8 h, and freezing a reaction solution in a refrigerator for 16 h; filtering out the solids, washing with cold ethanol (60 mL), and draining; and directly putting obtained yellow solids into reaction without drying;

adding 80% of formic acid (1000 mL) into the 2 L three-necked flask, cooling to below 0° C. by the ice-salt bath, then adding the above yellow crystals in batches, and keeping the internal temperature below 5° C.; reacting for 1 h under ice bath conditions after the end of adding and reacting at room temperature for 1 h; then performing heating and reflux reaction for 4 h; cooling to room temperature; removing a solvent by concentration; diluting obtained residues with water (1000 mL); regulating the pH to about 9 by using sodium carbonate solids, and extracting with ethyl acetate (1000 mL+500 mL×2); mixing organic phases, and drying with anhydrous sodium sulfate; performing decompression concentration and drying on filtrate to obtain light green solids, and stirring and washing for 16 h by using petroleum ether: ethyl acetate=20:1 (V:V) (500 mL); filtering, draining, and washing a filter cake with the petroleum ether (100 mL); and performing vacuum drying on the filter cake at the temperature of 40° C. for 8 h to obtain 24 g of light green solid powder.

MS: C12H7Br2N5 M.W.=381, and the height ratio of 378: 380:382 (M−H peak) is detected to be 1:2:1, which is in line with the number of atoms and the isotopic abundance ratio of Br.

The fourth step: preparation of tri[5-(4,4'-dibromo-2,2'-bipyridine-6-yl)-1,2,4-1H-triazole]terbium (III) (compound 13) and fluorescence emission spectrum test Dissolving the compound 11 (11.4 g) and terbium (II) chloride hexahydrate (3.7 g) respectively in 50 mL of a mixed solvent of ethylene glycol:water (V:V)=1:3 to prepare a solution E and a solution F; adding 1.2 g of sodium hydroxide into the solution E, and stirring to react for half an hour; then dropping the solution F into a reaction flask of the solution E, and stirring at room temperature to react for 16 h; and reducing pressure for evaporation after the end of reaction to remove the solvent, performing vacuum drying on the solids at the temperature of 50° C. for 3 h to obtain 10.5 g of yellow green powder.

MS: [M+1] 1299.4, TbC36H18Br6N15 M.W.=1298, and the peak height ratio of M+H peak 1297:1299:1301 is detected to be in line with the isotopic abundance ratio of complex molecules.

Through fluorescence emission spectrum test, we can know that the fluorescence emission wavelengths of the tri[5-(4,4'-dibromo-2,2'-bipyridine-6-yl)-1,2,4-1H-triazole]terbium (III) are 495 nm, 546 nm, 585 nm and 627 nm.

Embodiment 4

Synthesis of tri[5-(4,4'-dimethyl-2,2'-bipyridine-6-yl)-1,2,4-1H-triazole]europium (III) (compound 19) and fluorescence emission spectrum test The first step: preparation of N-oxo-4,4'-dimethyl-2,2'-bipyridine (compound 15)

Referring to the synthesis method of the compound 9, light yellow crystals, namely N-oxo-4,4'-dimethyl-2,2'-bipyridine (compound 15, 89 g) can be prepared from 4,4'-dimethyl-2,2'-bipyridine (compound 14, 100 g).

$^1$H NMR (CDCl$_3$ ppm) δ2.36 (3H, s), 2.41 (3H, s), 6.98-7.20 (2H, m), 7.96 (1H, m), 8.22 (1H, d), 8.58 (1H, d), 8.78 (1H, m).

Elementary analysis Anal. Calcd. For C12H12N2O: C, 71.98; H, 6.04; N, 13.99. Found: C, 71.88; H, 6.01; N, 14.03.

The second step: preparation of 6-cyano-4,4'-dimethyl-2,2'-bipyridine (compound 16)

Referring to the synthesis method of the compound 10, yellow solids, namely 6-cyano-4,4'-dimethyl-2,2'-bipyridine (compound 16, 66 g) can be prepared from N-oxo-4,4'-dimethyl-2,2'-bipyridine (compound 15, 80 g).

The third step: preparation of 5-(4,4'-dimethyl-2,2'-bipyridine-6-yl)-1,2,4-1H-triazole (compounds 17 and 18)

Referring to the synthesis method of the compound 11, earth yellow solid powder 5-(4,4'-dimethyl-2,2'-bipyridine-6-yl)-1,2,4-1H-triazole (compounds 17 and 18, 31 g) can be prepared from the compound 16 (50 g).

MS: C14H13N5 M.W.=251, and 252 (M+H peak) and 274 (M+Na peak) are detected.

The fourth step: preparation of tri[5-(4,4'-dimethyl-2,2'-bipyridine-6-yl)-1,2,4-1H-triazole]europium (III) (compound 19) and fluorescence emission spectrum test Dissolving the compound 17 (7.6 g) and europium (III) chloride hexahydrate (3.9 g) respectively in 50 mL of a mixed solvent of ethanol:water (V:V)=1:2 to prepare a solution G and a solution H; adding 1.2 g of sodium hydroxide into the solution G and stirring to react for half an hour; then dropping the solution H into a reaction flask of the solution G, and stirring at room temperature to react for 20 h; and reducing pressure for evaporation after the end of reaction to remove the solvent, performing vacuum drying on the solids at the temperature of 50° C. for 3 h to obtain 9.2 g of yellow powder.

MS: [M+1] 904.3, EuC42H36N15 M.W.=902, and the peak height ratio of M+H peak 902:904 is detected to be close to the isotopic abundance ratio of Eu, namely 1:1.

Through fluorescence emission spectrum test, we can know that the fluorescence emission wavelengths of the tri[5-(4,4'-dibromo-2,2'-bipyridine-6-yl)-1,2,4-1H-triazole]europium (III) are 595 nm and 617 nm.

Embodiment 5

Synthesis of tri[3-bromo-5-(2,2'-bipyridine-6-yl)-1,2,4-1H-triazole]terbium (III) (compound 21) and fluorescence emission spectrum test 5-(2,2'-bipyridine-6-yl)-1,2,4-1H-triazole (compound 4, 20 g) is prepared by with reference to embodiment 1 to be used as raw material.

The first step: preparation of 3-bromo-5-(2,2'-bipyridine-6-yl)-1,2,4-1H-triazole (compound 20)

Adding 5-(2,2'-bipyridine-6-yl)-1,2,4-1H-triazole (compound 4, 20 g) and water (300 mL) into a 1 L three-necked flask, uniformly stirring and slowly dropping 10M of NaOH solution to gradually dissolve the compound 4; regulating the pH=12, and enabling the solution to become clear; dropping 13.6 mL of liquid bromine (43.6 g) to react, simultaneously dropping 10M of NaOH solution to keep the pH of a reaction solution=12, and stirring to react for 3 h; regulating the pH to 3-4 by using 6M of hydrochloric acid after the end of reaction to obtain a crude product; and filtering, recrystallizing by using ethanol, and performing vacuum drying to obtain 14.2 g of yellow solids, namely 3-bromo-5-(2,2'-bipyridine-6-yl)-1,2,4-1H-triazole (compound 20).

MS: C12H8BrN5 M.W.=302, and the peak height ratio of M+H peak 302:304 is detected to be close to the isotopic abundance ratio of Br, namely 1:1.

The second step: preparation of tri[3-bromo-5-(2,2'-bipyridine-6-yl)-1,2,4-1H-triazole]terbium (III) (compound 21) and fluorescence emission spectrum test Dissolving the compound 20 (9.1 g) and terbium (III) chloride hexahydrate (3.7 g) respectively in 50 mL of a mixed solvent of 1,3-propylene glycol:water (V:V)=1:3 to prepare a solution I and a solution J; adding 1.2 g of sodium hydroxide into the solution I, and stirring to react for half an hour; then dropping the solution J into a reaction flask of the solution I, and stirring at room temperature to react for 24 h; and reducing pressure for evaporation after the end of reaction to remove the solvent, performing vacuum drying on the solids at the temperature of 50° C. for 3 h to obtain 10.1 g of yellow powder.

Figure 3:
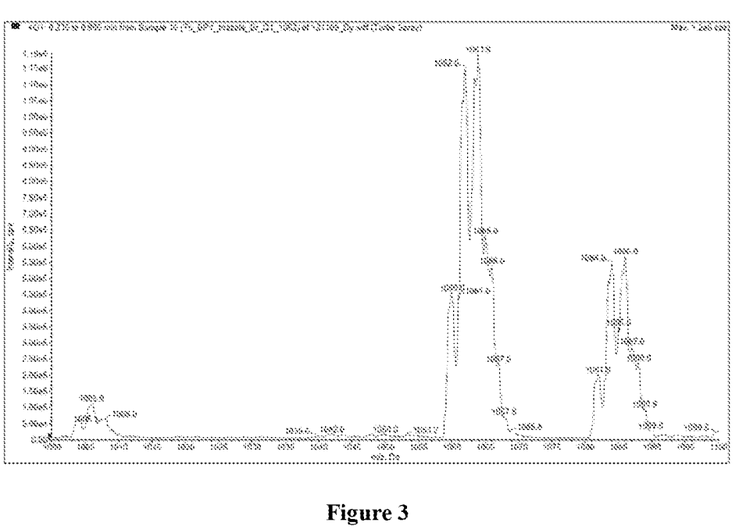
FIG. 3 is a mass spectrogram of tri[3-bromo-5-(2,2'-bipyridine-6-yl)-1,2,4-1H-triazole]terbium (II).

Ms: [M+1] 1063.9, TbC36H21Br3N15 M.W.=1062 and the peak height ratio of M+H peak 1062:1064 is detected to be in line with the isotopic abundance ratio of complex molecules. The mass spectrogram is as shown in FIG. 3.

Through fluorescence emission spectrum test, we can know that the fluorescence emission wavelengths of the tri[3-bromo-5-(2,2'-bipyridine-6-yl)-1,2,4-1H-triazole]terbium (III) are 493 nm, 545 nm, 585 nm and 626 nm.

Embodiment 6

Synthesis of tri[3-trifluoromethyl-5-(2,2'-bipyridine-6-yl)-1,2,4-1H-triazole]europium (III) (compound 24) and fluorescence emission spectrum test Referring to the method of embodiment 1 or embodiment 3, 6-cyano-2,2'-bipyridine (compound 3, 70 g) can be prepared as reaction raw material The first step: preparation of 3-trifluoromethyl-5-(2, 2'-bipyridine-6-yl)-1,2,4-1H-triazole (compounds 22 and 23)

Adding the compound 3 (70 g), ethanol (500 mL), water (200 mL) and hydrazine hydrate (80%, 200 mL) into the 2 L three-necked flask, stirring at room temperature to react for 8 h, and freezing a reaction solution in a refrigerator for 16 h; filtering out solids, washing with cold ethanol (100 mL), and draining; and directly putting obtained needle-like light yellow crystals into reaction without drying; adding trifluoroacetic acid (400 mL) into the 1 L three-necked flask, cooling to below 0° C. by the ice-salt bath, then adding the above solids in batches, and keeping the internal temperature below 5° C.; reacting for 2 h under ice bath conditions after the end of adding; then performing heating and reflux reaction for 4 h; cooling to room temperature; removing a solvent by concentration; diluting obtained residues with water (2000 mL); regulating the pH to about 9 by using sodium carbonate solids, and extracting with ethyl acetate (1000 mL+400 mL×2); mixing organic phases, drying with anhydrous sodium sulfate and decoloring by using activated carbon; filtering out a drying agent, performing decompression concentration and drying to obtain white solids, and stirring and washing for 16 h by using petroleum ether:ethyl acetate=1:1 (V:V) (500 mL); filtering, draining, and washing a filter cake with the petroleum ether (200 mL); and performing vacuum drying on the filter cake at the temperature of 40° C. for 8 h to obtain 54 g of white solid powder.

$^1$HNMR (300 MHz, DMSO), ppm: 7.55 (1H, t), 8.09 (1H, t), 8.19 (2H, d), 8.58 (1H, t), 8.75 (1H, d) and 8.93 (1H, d).

MS: C13H8F3N5 M.W.=291, and 292 (M+H peak) and 314 (M+Na peak) are detected.

The second step: preparation of tri[3-trifluoromethyl-5-(2,2'-bipyridine-6-yl)-1,2,4-1H-triazole]europium (III) (compound 24) and fluorescence emission spectrum test

Dissolving the compound 22 (8.7 g) and europium (III) chloride hexahydrate (3.9 g) respectively in 50 mL of a mixed solvent of ethylene glycol:water (V:V)=1:1 to prepare a solution K and a solution L; adding 1.2 g of sodium hydroxide into the solution K, and stirring to react for half an hour; then dropping the solution L into a reaction flask of the solution K, and stirring at room temperature to react for 16 h; and reducing pressure for evaporation after the end of reaction to remove the solvent, performing vacuum drying on the solids at the temperature of 50° C. for 3 h to obtain 9.5 g of light yellow powder.

MS: [M+1] 1024.3, EuC39H21F9N15 M.W.=1022, and the peak height ratio of M+H peak 1022:1024 is detected to be close to the isotopic abundance ratio of Eu, namely 1:1.

Through fluorescence emission spectrum test, we can know that the fluorescence emission wavelengths of the tri[3-trifluoromethyl-5-(2,2'-bipyridine-6-yl)-1,2,4-1H-triazole]europium (III) are 593 nm and 618 nm.

Embodiment 7

Synthesis of tri[3-trifluoromethyl-5-(2,2'-bipyridine-6-yl)-1,2,4-1H-triazole]neodymium (III) (compound 25) and fluorescence emission spectrum test Dissolving the compound 22 (8.7 g) prepared in embodiment 6 and neodymium nitrate (3.3 g) respectively in 50 mL of a mixed solvent of ethanol:water (V:V)=1:3 to prepare a solution M and a solution N; adding 1.2 g of sodium hydroxide into the solution M, and stirring to react for half an hour, then dropping the solution N into a reaction flask of the solution M, and stirring at room temperature to react for 16 h; and reducing pressure for evaporation after the end of reaction to remove the solvent, performing vacuum drying on the solids at the temperature of 50° C. for 3 h to obtain 9.8 g of yellow powder.

MS: [M+1] 1015.4, NdC39H21F9N15 M.W.=1014, and M+H peak 1015 and M+Na peak 1037 are detected.

Through fluorescence emission spectrum test, we can know that the fluorescence emission wavelength of the tri[3-trifluoromethyl-5-(2,2'-bipyridine-6-yl)-1,2,4-1H-triazole]neodymium (III) is 1062 nm.

Embodiment 8

Synthesis of tri[3-trifluoromethyl-5-(2,2'-bipyridine-6-yl)-1,2,4-1H-triazole]samarium (III) (compound 26) and fluorescence emission spectrum test

Embodiment 9

Synthesis of tri[3-trifluoromethyl-5-(2,2'-bipyridine-6-yl)-1,2,4-1H-triazole]terbium (III) (compound 27) and fluorescence emission spectrum test Dissolving the compound 22 (8.7 g) prepared in embodiment 6 and samarium (III) chloride hexahydrate (3.6 g) respectively in 50 mL of a mixed solvent of ethylene glycol:water (V:V)=1:2 to prepare a solution O and a solution P; adding 1.2 g of sodium hydroxide into the solution O, and stirring to react for half an hour; then dropping the solution P into a reaction flask of the solution O, and stirring to react at room temperature for 48 h; and reducing pressure for evaporation after the end of reaction to remove the solvent, performing vacuum drying on the solids at the temperature of 50° C. for 4 h to obtain 10.5 g of light yellow powder.

MS: [M+1] 1020.3, SmC39H21F9N15 M.W.=1020, and the peak height ratio of M+H peak 1020:1023 is detected to be close to the isotopic abundance ratio of Sm.

Through fluorescence emission spectrum test, we can know that the fluorescence emission wavelength of the tri[3-trifluoromethyl-5-(2,2'-bipyridine-6-yl)-1,2,4-1H-triazole] samarium (III) is 642 nm.

Dissolving the compound 22 (8.7 g) prepared in embodiment 6 and terbium (III) chloride hexahydrate (3.7 g) in 50 mL of mixed solvent of 1,3-propylene glycol:water (V:V) =1:3 to prepare a solution Q and a solution R: adding 1.2 g of sodium hydroxide into the solution Q, and stirring to react for half an hour: then dropping the solution R into a reaction flask of the solution Q, and stirring at room temperature to react for 16 h; and evaporation after the end of reaction to remove the solvent, performing vacuum drying on the solids at the temperature of 50° C. for 3 h to obtain 9.6 g of yellow green powder.

MS: [M+1] 1030.2, TbC39H21F9N15 M.W.=1029, and the peak height ratio of M+H peak 1030:1031 is detected to be close to the isotopic abundance ratio of Tb, namely 2:1.

Through fluorescence emission spectrum test, we can know that the fluorescence emission wavelengths of the tri[3-trifluoromethyl-5-(2,2'-bipyridine-6-yl)-1,2,4-1H-triazole] terbium (III) are 492 nm, 545 nm, 583 nm and 621 nm.

Embodiment 10

Synthesis of tri[3-trifluoromethyl-5-(2,2'-bipyridine-6-yl)-1,2,4-1H-triazole]dysprosium (III) (compound 28) and fluorescence emission spectrum test

Dissolving the compound 22 (8.7 g) prepared in embodiment 6 and dysprosium perchlorate (4.6 g) respectively in 50 mL of a mixed solvent of 1,3-propylene glycol:water (V:V)=1:1 to prepare a solution S and a solution T; adding 1.2 g of sodium hydroxide into the solution S, and stirring to react for half an hour; then dropping the solution T into a reaction flask of the solution S, and stirring at room temperature to react for 24 h; and reducing pressure for evaporation after the end of reaction to remove the solvent, performing vacuum drying on the solids at the temperature of 50° C. for 4 h to obtain 10.1 g of earth yellow powder.

MS: [M+1] 1034.3, DyC39H21F9N15 M.W.=1033, and the peak height ratio of M+H peak 1033:1034:1035 is detected to be close to the isotopic abundance ratio of Dy, namely 1:1:1.

Through fluorescence emission spectrum test, we can know that the fluorescence emission wavelength of the tri[3-trifluoromethyl-5-(2,2'-bipyridine-6-yl)-1,2,4-1H-triazole]dysprosium (III) is 573 nm.

Embodiment 11

Synthesis of tri[3-trifluoromethyl-5-(2,2'-bipyridine-6-yl)-1,2,4-1H-triazole]thulium (III) (compound 29) and fluorescence emission spectrum test Dissolving the compound 22 (8.7 g) prepared in embodiment 6 and thulium nitrate (3.5 g) respectively in 50 mL of a mixed solvent of 1,2-propylene glycol:water (V:V)=1:3 to prepare a solution U and a solution V; adding 1.2 g of sodium hydroxide into the solution U, and stirring to react for half an hour; then dropping the solution V into a reaction flask of the solution U, and stirring at room temperature to react for 48 h; and reducing pressure for evaporation after the end of reaction to remove the solvent, performing vacuum drying on the solids at the temperature of 50° C. for 4 h to obtain 9.3 g of yellow powder.

Figure 4:
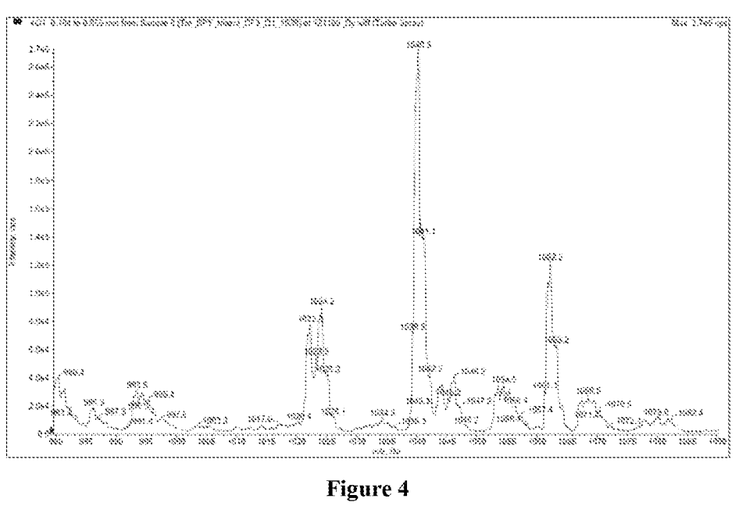
FIG. 4 is a mass spectrogram of tri[3-trifluoromethyl-5-(2,2'-bipyridine-6-yl)-1,2,4-1H-triazole]thulium (III).

MS: [M+1] 1040.3, TmC39H21F9N15 M.W.=1039, and M+H peak 1040 and M+Na peak 1062 are detected. The mass spectrogram is as shown in FIG. 4.

Through fluorescence emission spectrum test, we can know that the fluorescence emission wavelength of the tri[3-trifluoromethyl-5-(2,2'-bipyridine-6-yl)-1,2,4-1H-triazole]thulium (III) is 467 nm.

Embodiment 12

Synthesis of tri[3-phenyl-5-(2,2'-bipyridine-6-yl)-1,2,4-1H-triazole]europium (III) (compound 32) and fluorescence emission spectrum test Referring to the method of embodiment 1 or embodiment 3,6-cyano-2,2'-bipyridine (compound 3, 70 g) can be prepared as reaction raw material The first step: preparation of 3-phenyl-5-(2,2'-bipyridine-6-yl)-1,2,4-1H-triazole (compounds 30 and 31)

Adding the compound 3 (70 g), ethanol (500 mL), water (200 mL) and hydrazine hydrate (80%, 200 mL) into the 2 L three-necked flask, stirring at room temperature to react for 8 h, and freezing a reaction solution in a refrigerator for 16 h; filtering out solids, washing with cold ethanol (100 mL), and draining; directly putting obtained needle-like light yellow crystals into reaction without drying; filtering out the solids, washing with cold ethanol (100 mL) and draining; directly putting obtained needle-like light yellow crystals into the reaction without drying;

adding the above solids, toluene (500 mL) and triethylamine (60 g) into the 2 L three-necked flask, cooling to below 0° C. by the ice-salt bath, then dropping benzoyl chloride (72 g), and keeping the internal temperature below 5° C.; reacting for 2 h under ice bath conditions after the end of adding; turning to room temperature to react for 4 h; adding petroleum ether (1500 mL), stirring, and further adding 1 L of water, and stirring for half an hour, then filtering and draining to obtain white solids; transferring the solids into the 2 L three-necked flask, adding the toluene (1000 mL) and p-toluenesulfonic acid monohydrate crystals (8.7 g), and performing heating, reflux and water separation reaction for 24 h; removing a solvent by concentration, adding water (1000 mL), and then regulating the pH to 8-9 by using sodium carbonate solids; extracting with ethyl acetate (1000 mL+400 mL×2); mixing organic phases, drying with anhydrous sodium sulfate and decoloring by using activated carbon; filtering out a drying agent, increasing pressure for concentration and drying to obtain white solids, and recrystallizing by using petroleum ether:ethyl acetate=3:1 (V:V) (800 mL); and filtering, draining, and performing vacuum drying on a filter cake at the temperature of 40° C. for 8 h to obtain 68 g of white solid powder.

$^1$HNMR (300 MHz, DMSO), ppm: 7.56 (3H, m), 7.69, t), 8.08 (1H, t), 8.22-8.14 (4H, m), 8.62 (1H, t), 8.75 (1H, d), 8.93 (1H, d) and 14.9 (1H, brs).

MS: C18H13N5 M.W.=299, and 300 (M+H peak) and 322 (M+Na peak) are detected.

The second step: preparation of tri[3-phenyl-5-(2,2'-bipyridine-6-yl)-1,2,4-1H-triazole]europium (III) (compound 32) and fluorescence emission spectrum test

Dissolving the compound 30 (9.0 g) and europium (III) chloride hexahydrate (3.7 g) respectively in 50 mL of a mixed solvent of 2-methoxyethanol:water (V:V)=1:3 to prepare a solution W and a solution X; adding 1.2 g of sodium hydroxide into the solution W, and stirring to react for half an hour; then dropping the solution X into a reaction flask of the solution W, and stirring at room temperature to react for 16 h; and reducing pressure for evaporation after the end of reaction to remove the solvent, performing vacuum drying on the solids at the temperature of 50° C. for 3 h to obtain 9.8 g of light yellow powder.

MS: [M+1] 1048.4, EuC48H36N15 M.W.=1046, and the peak height ratio of M+H peak 1046:1048 is detected to be close to the isotopic abundance ratio of Eu, namely 1:1.

Through fluorescence emission spectrum test, we can know that the fluorescence emission wavelengths of the tri[3-phenyl-5-(2,2'-bipyridine-6-yl)-1,2,4-1H-triazole]europium (III) are 594 nm and 619 nm.

Embodiment 13

Synthesis of tri[3-phenyl-5-(2,2'-bipyridine-6-yl)-1,2,4-1H-triazole]terbium (III) (compound 33) and fluorescence emission spectrum test Dissolving the compound 30 (9.0 g) prepared in embodiment 12 and terbium (III) chloride hexahydrate (3.7 g) respectively in 50 mL of a mixed solvent of 2-eyhoxyethanol: water (V:V)=1:3 to prepare a solution Y and a solution Z; adding 1.2 g of sodium hydroxide into the Y solution, and stirring to react for half an hour; then dropping the Z solution into a reaction flask of the Y solution, and stirring at room temperature to react for 16 h; and reducing pressure for evaporation after the end of reaction to remove the solvent, performing vacuum drying on the solids at the temperature of 50° C. for 3 h to obtain 9.9 g of yellow powder.

MS: [M+1] 1054.2, TbC48H36N15 M.W.=1053, and the peak height ratio of M+H peak 1054:1055 is detected to be close to the isotopic abundance ratio of Tb, namely 2:1.

Through fluorescence emission spectrum test, we can know that the fluorescence emission wavelengths of the tri[3-phenyl-5-(2,2'-bipyridine-6-yl)-1,2,4-1H-triazole]terbium (III) are 488 nm, 545 nm, 590 nm and 623 nm.

The invention claimed is:

1. A bipyridine triazole type rare earth complex $LnL_3$, represented by structural formulas as shown in Formula 1:

Formula 1 wherein $R_1$ is hydrogen, halogen, an alkane group or an aromatic hydrocarbon group; $R_2$ is hydrogen, halogen, an alkane group or an aromatic hydrocarbon group; $R_3$ is hydrogen, halogen, methyl, trifluoromethyl or phenyl; and central rare earth ion Ln is any one of yttrium, lanthanum, cerium, praseodymium, neodymium, samarium, europium, gadolinium, terbium, dysprosium, holmium, erbium, thulium, ytterbium and lutetium.

2. A preparation method of the bipyridine triazole type rare earth complex according to claim 1:

a) oxidizing a bipyridine derivative represented by Formula 2 by an oxidant to generate a bipyridine type nitrogen oxide;

Formula 2 b) performing a cyano-substitution reaction on the bipyridine type nitrogen oxide to obtain a 6-cyano-bipyridine derivative;

c) enabling the 6-cyano-bipyridine derivative to react with a hydrazine and a carboxylic acid derivative for cyclization, thus obtaining a bipyridine triazole type compound; and d) enabling a rare earth metal salt to react with the bipyridine triazole type compound to generate the bipyridine triazole type rare earth complex $LnL_3$.

3. The preparation method of the bipyridine triazole type rare earth complex according to claim 2, wherein the oxidant in step a) is a m-chloroperoxybenzoic acid or hydrogen peroxide solution; a molar ratio of the oxidant to the bipyridine derivative is not less than 1:1; a reaction temperature is between room temperature and 110° C.; and a solvent is a carboxylic acid or an alkyl halide.

4. The preparation method of the bipyridine triazole type rare earth complex according to claim 2, wherein, in step b), a cyano reagent is NaCN, KCN, CuCN, $Zn(CN)_2$ or $(CH_3)_3SiCN$; a reaction temperature is less than 80° C.; and a reaction time is 1 to 7 days.

5. The preparation method of the bipyridine triazole type rare earth complex according to claim 2, wherein, in step c), the hydrazine and a 6-cyano-2,2'-bipyridine derivative react in a mixed solvent of alcohol and water in a volume ratio of 1:0 to 0:1 to obtain a reactant, then the reactant reacts with a carboxylic acid, an acid anhydride, an acyl chloride or an ester in a halogenated alkane, ester, aromatic hydrocarbon, alcohol, acid or ether solvent for cyclization, the amount of the hydrazine used is not less than 1.0 equivalent, the amount of the carboxylic acid, acid anhydride, acyl chloride or ester used is not less than 1.0 equivalent; and a reaction temperature ranges from room temperature to a reflux temperature according to different reaction substrates.

6. The preparation method of the bipyridine triazole type rare earth complex according to claim 2, wherein, in step c), a 6-cyano-2,2'-bipyridine derivative and an acylhydrazine directly react in a halogenated alkane, ester, aromatic hydrocarbon, alcohol, acid or ether solvent for cyclization; and a reaction temperature ranges from room temperature to a reflux temperature according to different reaction substrates.

7. The preparation method of the bipyridine triazole type rare earth complex according to claim 2, wherein, in step d), the rare earth metal salt is dissolved in water and dropped into a solution of the bipyridine triazole type compound and a water-soluble organic solvent of an alkali to start a reaction, a temperature is controlled at 0° C.-100° C., the reaction is continuously performed for 1 to 48 hours after the end of dropping, and a product is filtered and recrystallized to obtain the bipyridine triazole type rare earth complex $LnL_3$.

8. The preparation method of the bipyridine triazole type rare earth complex according to claim 7, wherein, the rare earth metal salt is selected from chloride, bromide, fluoride, iodide, nitrate, sulfate, perchlorate, phosphate, carboxylate, sulfonate, fluoroborate and hexafluorophosphate of rare earth metals; the amount of the rare earth metal salt used is 1.0 equivalent, the amount of the bipyridine triazole derivative used is 2.0-4.0 equivalents, the alkali is an inorganic alkali or an organic alkali, and the amount used is not less than 1.0 equivalent; and the organic solvent is an alcohol.

* * * * *